(12) United States Patent
Gutiérrez Fuentes et al.

(10) Patent No.: US 9,296,780 B2
(45) Date of Patent: Mar. 29, 2016

(54) PROCESS FOR ALKYNYLATING 16-SUBSTITUTED-17-KETO STEROIDS

(71) Applicants: CRYSTAL PHARMA, S. A. U., Boecillo-Valladolid (ES); THE POPULATION COUNCIL INC., New York, NY (US)

(72) Inventors: Luis Gerardo Gutiérrez Fuentes, Boecillo-Valladolid (ES); Celso Miguel Sandoval Rodriguez, Boecillo-Valladolid (ES)

(73) Assignees: Crystal Pharma, S.A.U., Valladolid (ES); Population Council Inc., New York, NY (US)

( * ) Notice: Subject to any disclaimer, the term of this patent is extended or adjusted under 35 U.S.C. 154(b) by 0 days.

(21) Appl. No.: 14/367,886

(22) PCT Filed: Dec. 19, 2012

(86) PCT No.: PCT/EP2012/076095
§ 371 (c)(1),
(2) Date: Jun. 20, 2014

(87) PCT Pub. No.: WO2013/092668
PCT Pub. Date: Jun. 27, 2013

(65) Prior Publication Data
US 2015/0005518 A1    Jan. 1, 2015

Related U.S. Application Data

(60) Provisional application No. 61/580,010, filed on Dec. 23, 2011.

(30) Foreign Application Priority Data

Dec. 23, 2011 (EP) .................................... 11382395

(51) Int. Cl.
*C07J 7/00* (2006.01)
*C07J 31/00* (2006.01)
*C07J 51/00* (2006.01)
*C07J 1/00* (2006.01)
*C07J 75/00* (2006.01)

(52) U.S. Cl.
CPC ............... *C07J 75/00* (2013.01); *C07J 1/0011* (2013.01); *C07J 7/00* (2013.01); *C07J 7/009* (2013.01); *C07J 7/0075* (2013.01); *C07J 31/006* (2013.01); *C07J 51/00* (2013.01)

(58) Field of Classification Search
CPC .................................. C07J 7/00; C07J 1/0011
See application file for complete search history.

(56) References Cited

U.S. PATENT DOCUMENTS 4,614,621 A * 9/1986 VanRheenen ................. 552/528

FOREIGN PATENT DOCUMENTS

| WO | 93/15103 | 8/1993 |
|---|---|---|
| WO | WO 93/15103 A2 * | 8/1993 |
| WO | 97/23498 | 7/1997 |

OTHER PUBLICATIONS

Zaragoza Dorwald, Side Reactions in Organic Synthesis, 2005, Wiley-VCH Verlag GmbH & Co. KGaA, Weinheim, Preface. p. IX.*
Hirschmann, Angewandte Chemie International Edition in English, 2003, 30(10), pp. 1278-1301.*
International Search Report dated Feb. 7, 2013 for PCT/EP2012/076095.
Wong, et al., "One-pot ethynylation and catalytic desilylation in synthesis of mestranol and levonorgestrel", Tetrahedron 66 (2010) 4068-4072.
Trost B., "Comprehensive organic synthesis", 1991, vol. 4, pp. 72-73, Elsevier, Amsterdam, The Netherlands.

* cited by examiner

*Primary Examiner* — Paul A Zucker
(74) *Attorney, Agent, or Firm* — Knobbe, Martens, Olson & Bear, LLP

(57) ABSTRACT

A process ethynylates 16-methylene-17-keto steroids to the corresponding 16-methylene-17α-ethynyl-17β-hydroxy steroids by treatment with silyl-protected lithium acetylides followed by further desilylation. The resulting products are useful intermediates in the preparation of several pharmaceutically active agents, such as e.g. Nestorone® or melengestrol acetate.

12 Claims, No Drawings

PROCESS FOR ALKYNYLATING 16-SUBSTITUTED-17-KETO STEROIDS

CROSS REFERENCE TO RELATED APPLICATIONS

This application is the U.S. National Phase of International Application No. PCT/EP2012/076095, filed Dec. 19, 2012, designating the U.S. and published as WO 2013/0092668 on Jun. 27, 2013 which claims the benefit of U.S. Provisional Patent Application No. 61/580,010, filed Dec. 23, 2011 and European Patent Application No. 11382395.9, filed Dec. 23, 2011.

FIELD OF THE INVENTION

The invention relates to a process for ethynylating 16-methylene-17-keto steroids to the corresponding 16-methylene-17α-ethynyl-17β-hydroxy steroids, which are useful intermediates in the preparation of several pharmaceutically active agents, such as e.g. Nestorone® or melengestrol acetate.

BACKGROUND OF THE INVENTION

Ethynylation of 17-keto steroids to produce commercially important 17α-ethynyl-17β-hydroxy steroids is well known to those skilled in the art. See, for example, U.S. Pat. Nos. 2,272,131, 2,843,609, 2,723,280, 3,275,666, 3,275,666, 2,877,240, 3,470,217, 4,041,055, 3,927,046, Steroids by Fieser and Fieser, Reinhold Publishing Co, New York, 1959, 557-591 and J. Am. Chem. Soc. 1956, 78, 2477.

A general method for this reaction consists in reacting the 17-keto steroid with dipotassium acetylide, which can be used with $\Delta^4$-3-keto steroids without having to protect the carbonyl group at position 3. However, this process is not suitable for 16-methylene-17-keto steroids due to the steric hindrance of these systems, which reduces the reactivity and induces the formation of different impurities.

Ethynylation of 16-methylene-17-keto steroids is commercially important because the resulting 16-methylene-17-α-ethynyl-17-β-hydroxy products are intermediates in the preparation of therapeutically valuable compounds, such as e.g. Nestorone® or melengestrol acetate.

Other metallo-acetylides, such as mono- and di-magnesium acetylides, have been used in the ethynylation of 16-methyl-17-keto steroids (U.S. Pat. No. 3,704,253), though low yields have been obtained (lower than 50%) due to the need of chromatographic purification and the formation of dimers as the main impurity. Example II in U.S. Pat. No. 3,704,253 discloses lower than 30% yield in the magnesium-acetylide addition to a 16-methylene-17-keto steroid.

Better results have been achieved using monolithium acetylide, which can be obtained by reacting acetylene with n-butyllithium at low temperature, preferably below −70° C. in dilute solution as reported by Midland in J. Org. Chem. 1975, 40, 2250. The use of monolithium acetylide in the preparation of ethynyl-carbinols is disclosed e.g. in Fieser & Fieser, reagents for Organic Chemistry Vol. 1, Wiley, New York, 1967, p 573.

However, monolithium acetylide easily decomposes to the corresponding dilithium acetylide (which is insoluble and precipitates) just by increasing the temperature or concentrating the solution. This is an important drawback in relation with its reactivity and availability in the reaction medium. Consequently, its use is limited to very low temperatures in order to keep the monolithium acetylide system (see U.S. Pat. Nos. 4,055,562, 4,567,001). This prevents its efficient application in more hindered systems such as 16-methylene derivatives.

To prevent formation of dilithium acetylide, complexing agents (e.g. ethylendiamine) able to stabilize monolithium acetylide are used. Monolithium acetylide-ethylenediamine complex is sold commercially. Nevertheless, complex formation highly reduces its reactivity. As a consequence, though ethynylation of reactive ketones can be achieved (U.S. Pat. No. 4,320,236), low yields are obtained in more sterically hindered systems such as 16-methyl-17-keto steroids (U.S. Pat. No. 3,704,253; Example 4).

This problem is partially solved by the use of more hindered amines (see U.S. Pat. No. 4,614,621), e.g. diisopropylamine (Example 1) or triethylamine (Example 13), allowing to perform the reaction at a temperature between −20 and −40° C. without decomposition of the monolithium acetylide. However, if reaction conditions are prolonged, dilithium acetylide is formed at a constant rate. No yields or purity data are mentioned in this document. This US patent, discloses the use of monolithium acetylide complexed with hindered amines in the synthesis of e.g. melengestrol acetate through the following sequence:

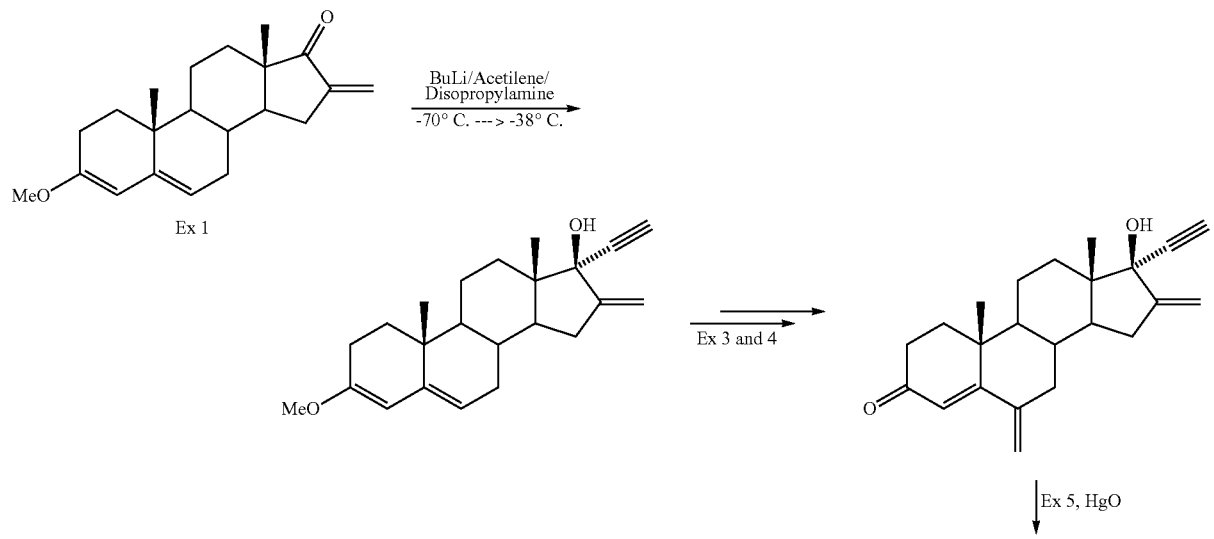

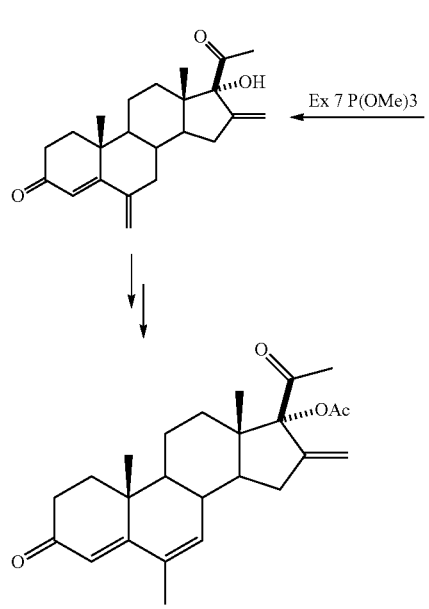

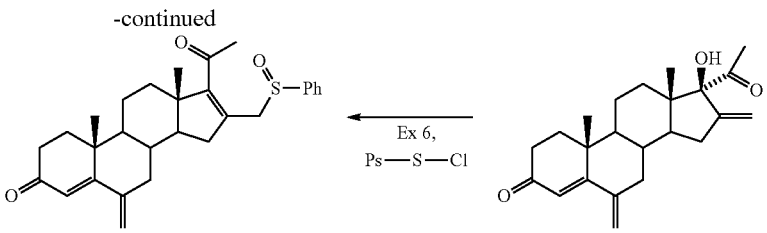

WO 97/23498 describes a similar synthetic process as above but on a compound having an ethyl group at position 18 and lacking the methyl radical at position 19 (Examples 4 and 5):

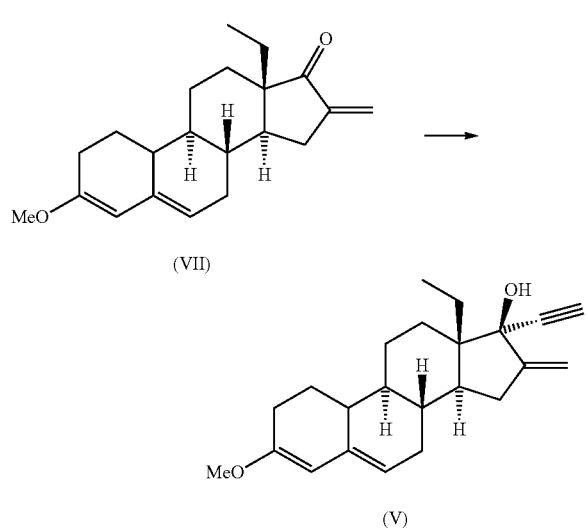

In this case, ethynylation is achieved by using a high excess of monolithium acetylide, generated in situ from nBuLi (7 mol) and gaseous acetylide at −70° C. The reaction is carried out at −40° C. for 2.5 h, giving rise to the ethynylated product with moderate yield (67%).

Use of lithium (trimethylsilyl)acetylide in the ethynylation of 17-keto steroids was disclosed in Tetrahedron 2010, 66, 4068-4072. Lithium (trimethylsilyl)acetylide was generated by reacting trimethylsilylacetylene with nBuLi at −40° C. and the ethynylated product was further desilylated by treatment with catalytic TBAF, giving rise to mestranol and levonorgestrel in 90%. However, these esteroids are not substituted at position 16 and are therefore more reactive and less prone to produce undesired side products than the corresponding 16-methylene substituted steroids.

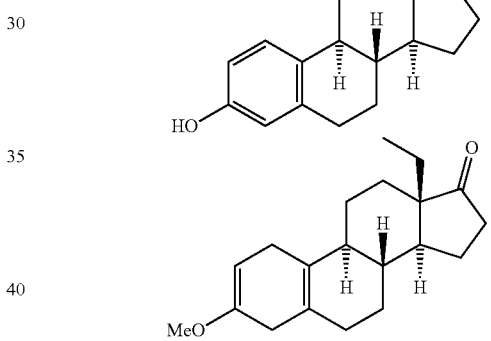

In general, reaction conditions disclosed in the prior art for the ehtynylation of 16-methyl- or 16-methylene-17-keto steroids refer to the use of magnesium acetylides (U.S. Pat. No. 3,275,666) that afford very poor yields, or the use of unstable lithium acetylide, which has to be generated in situ by reacting flammable acetylene gas with bases difficult to handle as BuLi at very low temperature (from −70 to −40° C.). Yields reported in the prior art for this type of 16-substituted systems are low or moderate (WO 97/23498, Examples 4 and 5) with the need in some cases of high excess of lithium acetylide.

As a consequence, it is still necessary to develop a process for the ethynylation of hindered steroids, such as 16-methylene-17-keto derivatives, that overcomes all or part of the problems associated with the known processes belonging to the state of the art. Specially, more efficient, easier and/or industrially applicable processes would be desirable.

Document WO 93/15103 refers to the synthesis of steroid intermediates through a process comprising ethynylation of 16-methyl-17-keto stereroids having a hydroxy or carbonate group at position 9. Use of lithium trimethylsilylacetylide as an alternative to lithium acetylide in this process is disclosed. No advantages of the use of the silyl-substituted compound are mentioned.

However, use of lithium trisubstitutedsilylacetylides in the ethynylation of 16-methylene-17-keto stereroids has not been reported in the prior art. Inventors have observed that lithium trisubstitutedsilylacetylides can be efficiently used in the preparation of 16-methylene-17-α-ethynyl-17-β-hydroxy compounds. In addition, inventors have surprisingly observed that the use of this alkynylating agent provides an improved process for obtaining 16-methylene-17-α-ethynyl-17-β-hydroxy compounds compared to the use of lithium acetylide or other ethynylating agents used in the prior art for preparing this type of compounds.

SUMMARY OF THE INVENTION

The invention faces the problem of providing an improved process for the ethynylation of 16-methylene-17-keto steroids. The inventors have surprisingly found that silyl-protected lithium acetylides can be efficiently used in the ethynylation of sterically hindered 16-methylene-17-keto steroids, affording the corresponding 16-methylene-17-α-ethynyl-17-β-hydroxy compounds in high yield, while avoiding the use of complex or non-industrially applicable experimental conditions. Additionally, the resulting compounds are obtained in high purity.

In particular, the inventors have observed e.g. that the addition of lithium (trimethylsilyl)acetylide to compound 3, followed by cleavage of the silyl group, leads to the corresponding 17-ethynyl product 4 in high yield (92%) and purity. Typical impurities in ethynylation processes, such as dimmers or di-ethynylated products, were not detected.

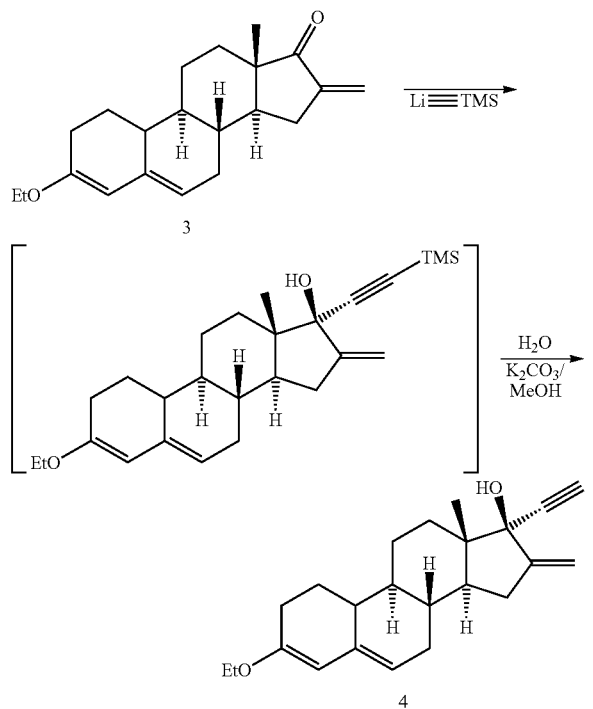

In contrast, reaction of compound 3 with magnesium acetylide resulted in partial deprotection of the enol ether in position 3, thus affording the di-ethynylated product at positions 3 and 17 as the main impurity. The desired product was obtained in yields lower than 50%.

Commercially available monolithium acetylide-ethylenediamine complex showed low reactivity against this system, giving rise to dimer formation when conditions were forced.

Use of sodium, potassium, magnesium and lithium acetylides under conditions similar to those reported in the previous prior art, afforded low yields (as much as 55%) of the desired product together with dimerization impurities resulting from the reaction of acetylide with two molecules of steroid and diethynylated products at positions 3 and 17. Double bond at position 16 could also react, leading to further impurities.

Consequently, the ethynylation process of the invention provides much higher yields than other prior art acetylide addition processes assayed on the same 16-methylene substituted substrate.

Thus, in a first aspect, the invention is directed to a process for the preparation of 16-methylene-17α-ethynyl-17β-hydroxy steroids, which comprises treating a 16-methylene-17-keto steroid with a compound of formula (I)

wherein each R is independently selected from substituted or unsubstituted $C_1$-$C_6$ alkyl, substituted or unsubstituted aryl and halogen, followed by desilylation of the corresponding 16-methylene-17α-silylethynyl-17β-hydroxy steroid.

In another aspect the invention is directed to an intermediate compound of formula (III):

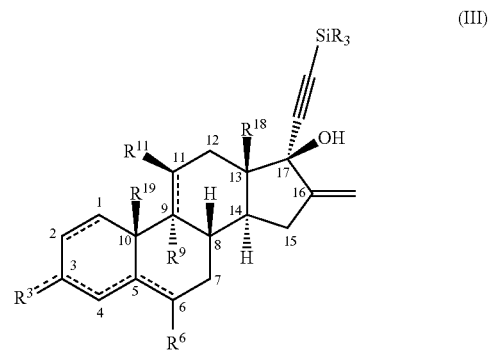

wherein
each R is independently selected from substituted or unsubstituted $C_1$-$C_6$ alkyl, substituted or unsubstituted aryl and halogen;
$R^3$ is selected from O or —$OR^1$, wherein $R^1$ is a substituted or unsubstituted $C_1$-$C_6$ alkyl; with the proviso that when $R^3$ is O then there are double bonds between $C_3$ and $R^3$ and between $C_4$ and $C_5$ and single bonds between $C_3$ and $C_4$ and between $C_5$ and $C_6$, and when $R^3$ is —$OR^1$ then there are single bonds between $C_3$ and $R^3$ and between $C_4$ and $C_5$ and double bonds between $C_3$ and $C_4$ and between $C_5$ and $C_s$;
$R^6$ is selected from H, substituted or unsubstituted $C_1$-$C_6$ alkyl, halogen and methylene (=$CH_2$); with the proviso that when $R^6$ is methylene then there is a double bond between $C_6$ and $R_6$ and a single bond between $C_5$ and $C_6$,
$R^9$ is selected from H and halogen, or is absent when there is a double bond between $C_9$ and $C_{11}$;
$R^{11}$ is selected from H, OH and halogen, or is absent when there is a double bond between $C_9$ and $C_{11}$;

$R^{18}$ is selected from methyl and ethyl;
$R^{19}$ is selected from H and methyl;
--- is a single or double bond.

DETAILED DESCRIPTION OF THE INVENTION

The term "alkyl" refers to a linear or branched alkane derivative containing from 1 to 6 ("$C_1$-$C_6$ alkyl"), preferably from 1 to 3 ("$C_1$-$C_3$ alkyl"), carbon atoms and which is bound to the rest of the molecule through a single bond. Illustrative examples of alkyl groups include methyl, ethyl, propyl, butyl, pentyl, hexyl, etc.

The term "cycloalkyl" refers to a radical derived from cycloalkane containing from 3 to 7 ("$C_3$-$C_7$ cycloalkyl"), preferably from 3 to 6 ("$C_3$-$C_6$ cycloalkyl") carbon atoms. Illustrative examples of cycloalkyl groups include cyclopropyl, cyclobutyl, cyclopentyl, cyclohexyl, etc.

The term "aryl" refers to an aromatic group having between 6 and 18, preferably between 6 and 10, more preferably 6 or 10 carbon atoms, comprising 1, 2 or 3 aromatic nuclei bound through a carbon-carbon bond or fused to one another. Illustrative examples of aryl groups include phenyl, naphthyl, diphenyl, indenyl, phenanthryl, etc.

The term "halogen" refers to bromine, chlorine, iodine or fluorine.

"Heterocyclyl" refers to a stable cyclic radical of 3 to 10 members, preferably a cycle of 5 or 6 members consisting of carbon atoms and from 1 to 5, preferably from 1 to 3, heteroatoms selected from nitrogen, oxygen and sulfur, and which may be completely or partially saturated or be aromatic ("heteroaryl"). In the present invention, the heterocyclyl can be a mono-, bi- or tricyclic system which may include fused ring systems. Illustrative examples of heterocyclyl groups include, for example, pyrrolidine, piperidine, piperazine, morpholine, tetrahydrofuran, benzimidazole, benzothiazole, furan, pyrrole, pyridine, pyrimidine, thiazole, thiophene, imidazole, indole, etc.

As understood in this technical area, there may be a certain degree of substitution in the aforementioned radicals. Therefore, there may be substitution in any of the groups of the present invention. The previous groups can be substituted in one or more available positions with one or more substituents. Said substituents include, for example and in non-limiting sense, $C_{1-6}$ alkyl, $C_{3-7}$ cycloalkyl, aryl, heterocyclyl, heteroaryl, halogen, —CN, $NO_2$, $CF_3$, —N($R_a$)($R_b$), —$OR_c$, —$SR_d$, —C(O)$R_e$, —C(O)O$R_f$, —C(O)N($R_g$)($R_h$), —OC(O)$R_i$; wherein $R_a$, $R_b$, $R_c$, $R_d$, $R_e$, $R_f$, $R_g$, $R_h$ and $R_i$ are independently selected from hydrogen, $C_1$-$C_6$ alkyl, aryl, heterocyclyl, heteroaryl and trifluoromethyl.

The term "organic solvent" includes for example cyclic and acyclic ethers (e.g. $Et_2O$, $iPr_2O$, 1,4-dioxane, tetrahydrofuran, methyltetrahydrofuran), hydrocarbonated solvents (e.g. pentane, hexane), halogenated solvents (e.g. dichloromethane, chloroform), aromatic solvents (e.g. toluene), esters (e.g. EtOAc), nitriles (e.g. acetonitrile), alcohols (e.g. methanol, ethanol, propanol) and mixtures thereof.

In a first aspect, the invention is directed to a process for the preparation of 16-methylene-17α-ethynyl-17β-hydroxy steroids, which comprises treating a 16-methylene-17-keto steroid with a compound of formula (I)

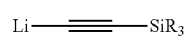
(I)

wherein each R is independently selected from optionally substituted $C_1$-$C_6$ alkyl, optionally substituted aryl and halogen,
followed by desilylation of the resulting 16-methylene-17α-silylethynyl-17β-hydroxy steroid.

After addition of the compound of formula (I) to the 16-methylene-17-keto steroid, the corresponding 16-methylene-17-α-silylethynyl-17β-hydroxy steroid is obtained. This compound can be isolated and further desilylated to yield the 16-methylene-17-α-ethynyl-17β-hydroxy steroid or, alternatively, it can be desilylated in situ, without isolation of the intermediate silylated product, to afford the 16-methylene-17-α-ethynyl-17β-hydroxy steroids in a "one-pot" process.

Therefore, in a particular embodiment, desylilation reaction is performed without isolation of the corresponding 16-methylene-17-α-silylethynyl-17-β-hydroxy steroid intermediate product.

In another embodiment, the corresponding 16-methylene-17-α-silylethynyl-17-β-hydroxy steroid intermediate product is isolated before the desilylation reaction.

Reaction of the 16-methylene-17-keto steroid with a compound of formula (I) is preferably performed in the presence of an organic solvent, preferably, an anhydrous organic solvent, such as for example a cyclic or acyclic ether (e.g. $Et_2O$, $iPr_2O$, 1,4-dioxane, tetrahydrofuran, methyltetrahydrofuran), a hydrocarbonated solvent (e.g. pentane, hexane), a halogenated solvent (e.g. dichloromethane, chloroform), an aromatic solvent (e.g. toluene) or mixtures thereof. Preferably the organic solvent is a cyclic or acyclic ether, such as $Et_2O$, $iPr_2O$, 1,4-dioxane, tetrahydrofuran, methyltetrahydrofuran or mixtures thereof. In a particular embodiment, the organic solvent is tetrahydrofuran. In the present application, the term anhydrous solvent refers to a solvent containing less than 500 ppm of water.

In a particular embodiment, this reaction is performed at a temperature lower than 30° C. In another embodiment, it is performed at a temperature of between −40 and +25° C., preferably between −10 and +5° C.

In a particular embodiment, the compound of formula (I) is present in an amount of from 1.0 to 5.0 equivalents with respect to the 16-methylene-17-keto steroid. Preferably from 1.0 to 4.0, more preferably from 1.1 to 2.0 equivalents.

In a particular embodiment, the compound of formula (I) is formed in situ by reacting a compound of formula (I')

(I')

wherein R is as defined above,
with a lithium base, such as for example, n-BuLi, n-hexyl-Lithium, s-BuLi, t-BuLi, LiN(i-Pr)$_2$, LiNEt$_2$, lithium 2,2,6,6-tetramethylpiperidine (LiTMP) or LiN(SiMe$_3$)$_3$ (LiHMDS). In a particular embodiment, the lithium base is a lithium amide base, such as e.g. LiN(i-Pr)$_2$, LiNEt$_2$, lithium 2,2,6,6-tetramethylpiperidine (LiTMP) or LiN(SiMe$_3$)$_3$ (LiHMDS). Preferably, it is LiHMDS.

In a particular embodiment, the compound of formula (I') is present in an amount of from 1.0 to 5.0 equivalents with respect to the 16-methylene-17-keto steroid. Preferably from 1.0 to 4.0, more preferably from 1.1 to 2.0 equivalents.

In a particular embodiment, the lithium base is present in an amount of from 1.0 to 5.0 equivalents with respect to the 16-methylene-17-keto steroid. Preferably from 1.1 to 4.0, more preferably from 1.3 to 2.5 equivalents.

Desylilation reaction of the intermediate 16-methylene-17-α-silylethynyl-17-β-hydroxy steroid can be carried out by methods known in the prior art (e.g. Green T W et al., "Protective Groups in Organic Synthesis", 3$^{rd}$ Edition (1999), Ed. John Wiley & Sons). In a particular embodiment, the desilylation is carried out using fluorine salts or bases in the presence of water, an organic solvent or mixtures thereof. Organic solvents such as e.g. cyclic or acyclic ethers (e.g. $Et_2O$, $iPr_{2O}$, 1,4-dioxane, tetrahydrofuran, methyltetrahydrofuran), hydrocarbonated solvents (e.g. pentane, hexane), halogenated solvents (e.g. dichloromethane, chloroform), aromatic solvents (e.g. toluene), esters (e.g. EtOAc), nitriles (e.g. acetonitrile), alcohols (e.g. methanol, ethanol, propanol) or mixtures thereof can be used. Fluorine salts such as pyridinium fluoride, potassium fluoride or ammonium fluoride (e.g. TBAF); or inorganic bases, such as sodium hydroxide, lithium hydroxide, potassium hydroxide or potassium carbonate can be used. In a particular embodiment, the desilylation reaction is carried out in the presence of an inorganic base, preferably potassium carbonate, and an organic solvent, preferably methanol.

In a particular embodiment, the desilylation reaction is performed at a temperature between −60 and +100° C. In another embodiment, it is performed at a temperature between −10 and +60° C., preferably between 10 and 35° C.

In a particular embodiment, each R is independently selected from $C_1$-$C_6$ alkyl, phenyl and Cl. In a further embodiment, each R is independently selected from methyl, ethyl, n-propyl, i-propyl, n-butyl, t-butyl, n-hexyl, Ph and Cl. Preferably, —$SiR_3$ is selected from $Et_3Si$—, $Me_3Si$—, $^iPr_3Si$—, $^nPr_3Si$—, $^nHex_3Si$—, $^tBu_3Si$—, $Ph_3Si$—, $Cl_3Si$—, $MeEt_2Si$—, $^tBuMe_2Si$—, $^tBuPh_2Si$—, $Cl^iPr_2Si$—, $ClMe_2Si$—, $MePh_2Si$—, $EtMe_2Si$—, $EtCl_2Si$—, $MeCl_2Si$—, $PhMe_2Si$— and $PhMeClSi$—. More preferably, —$SiR_3$ is selected from $Me_3Si$—, $Et_3Si$—, $^iPr_3Si$—, $PhMe_2Si$—, $^tBuMe_2Si$— and $^tBuPh_2Si$—. Still more preferably, —$SiR_3$ is selected from $Me_3Si$—, $^iPr_3Si$— and $PhMe_2Si$—.

In an embodiment of the invention, the 16-methylene-17-keto steroid is a compound of formula (II)

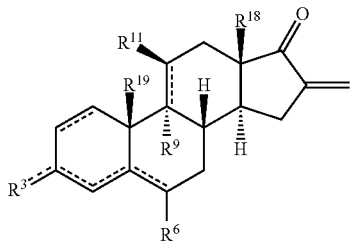

(II)

wherein
$R^3$ is selected from O and —$OR^1$, wherein $R^1$ is a substituted or unsubstituted $C_1$-$C_6$ alkyl; with the proviso that when $R^3$ is O then there are double bonds between $C_3$ and $R^3$ and between $C_4$ and $C_5$ and single bonds between $C_3$ and $C_4$ and between $C_5$ and $C_6$, and when $R^3$ is —$OR^1$ then there are single bonds between $C_3$ and $R^3$ and between $C_4$ and $C_5$ and double bonds between $C_3$ and $C_4$ and between $C_5$ and $C_s$;

$R^6$ is selected from H, substituted or unsubstituted $C_1$-$C_6$ alkyl, halogen and methylene (=$CH_2$); with the proviso that when $R^6$ is methylene then there is a double bond between $C_6$ and $R_6$ and a single bond between $C_s$ and $C_s$;
$R^9$ is selected from H and halogen, or is absent when there is a double bond between $C_9$ and $C_{11}$;
$R^{11}$ is selected from H, OH and halogen, or is absent when there is a double bond between $C_9$ and $C_{11}$;
$R^{18}$ is selected from methyl and ethyl;
$R^{19}$ is selected from H and methyl;
--- is a single or double bond.

Therefore in a particular embodiment, the invention refers to a process for the preparation of a compound of formula (IV)

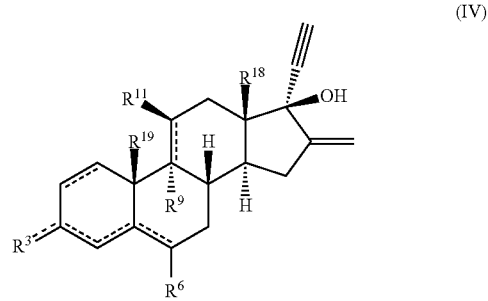

wherein $R^3$, $R^6$, $R^9$, $R^{11}$, $R^{18}$, $R^{19}$ and --- are as defined herein,
which comprises:
(a) reacting a compound of formula (II) as defined above with a compound of formula (I) as defined above to afford a compound of formula (III)

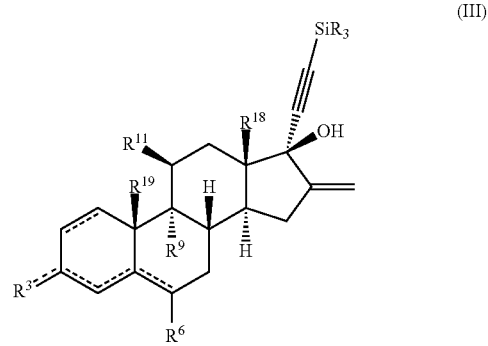

wherein R, $R^3$, $R^6$, $R^9$, $R^{11}$, $R^{18}$, $R^{19}$ and --- are as defined herein, and
(b) desilylating the resulting compound of formula (III) to afford the compound of formula (IV).

In a particular embodiment, the compound of formula (III) is isolated, and optionally purified, before subjecting it to step (b). In another embodiment, the compound of formula (III) is desilylated in situ, without prior isolation, to afford the compound of formula (IV) in a "one-pot" process.

In a particular embodiment, $R^3$ is a $OR^1$ group wherein $R^1$ is a $C_1$-$C_6$ alkyl, preferably a $C_1$-$C_3$ alkyl, more preferably it is selected from methyl and ethyl.

In a particular embodiment, $R^6$ is selected from H, halogen, methylene and $C_1$-$C_3$ alkyl, more preferably it is selected from H, F, methylene and methyl.

In a particular embodiment, $R^9$ is selected from H and halogen, more preferably it is selected from H and F.

In a particular embodiment, $R^{11}$ is selected from H, OH and halogen, more preferably it is selected from H and OH.

In another embodiment, there is a double bond between $C_9$ and $C_{11}$ and, therefore, $R^9$ and $R^{11}$ are absent.

In a particular embodiment, $R^{18}$ is selected from methyl and ethyl, more preferably it is methyl.

In a particular embodiment, $R^{19}$ is selected from H and methyl.

In a particular embodiment, $R^3$ is —$OR^1$ and there are single bonds between $C_3$ and $R^3$, between $C_4$ and $C_5$, and between $C_1$ and $C_2$ and double bonds between $C_3$ and $C_4$ and between $C_5$ and $C_6$.

In a particular embodiment, $R^3$ is O and there are double bonds between $C_3$ and $R^3$, between $C_4$ and $C_5$, and between $C_1$ and $C_2$ and single bonds between $C_3$ and $C_4$ and between $C_5$ and $C_6$.

In a particular embodiment, there is a single bond between $C_1$ and $C_2$.

In a particular embodiment, the compound of formula (II) is a compound of formula (IIa)

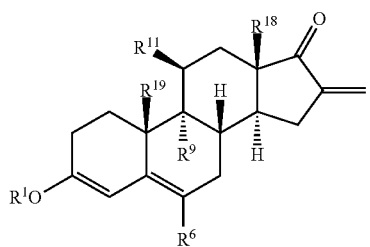

(IIa)

wherein $R^1$, $R^6$, $R^9$, $R^{11}$, $R^{18}$ and $R^{19}$ are as defined above.

In the compounds of formula (IIa), $R^1$ is preferably selected from $C_1$-$C_6$ alkyl; $R^6$ is preferably selected from H and methyl; $R^9$ is preferably H; $R^{11}$ is preferably H; $R^{18}$ is preferably methyl; and $R^{19}$ is preferably selected from H and methyl.

Still further preferred compounds of formula (II) are the following:

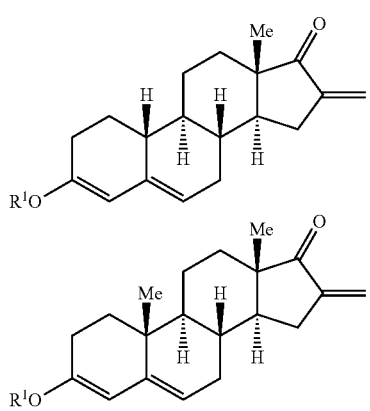

wherein $R^1$ is an optionally substituted $C_1$-$C_6$ alkyl, preferably a $C_1$-$C_3$ alkyl, more preferably it is selected from methyl and ethyl.

Consequently, in a particular embodiment, the compound of formula (III) is a compound of formula (IIIa) or (IIIa')

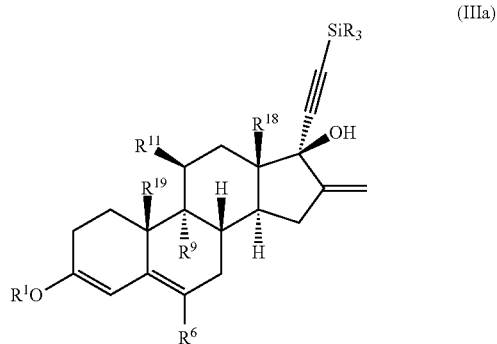

(IIIa)

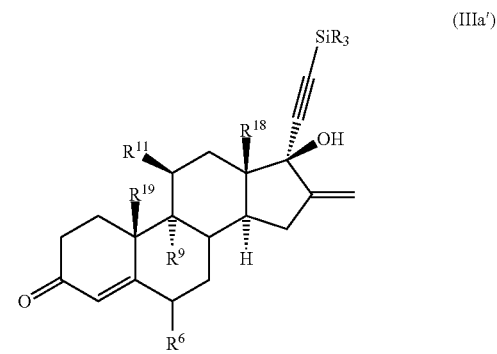

(IIIa')

wherein R, $R^1$, $R^6$, $R^9$, $R^{11}$, $R^{18}$ and $R^{19}$ are as defined above.

Further preferred embodiments for the compounds of formula (IIIa) and (IIIa') are as those defined previously for (IIa).

Still further preferred compounds of formula (III) are the following:

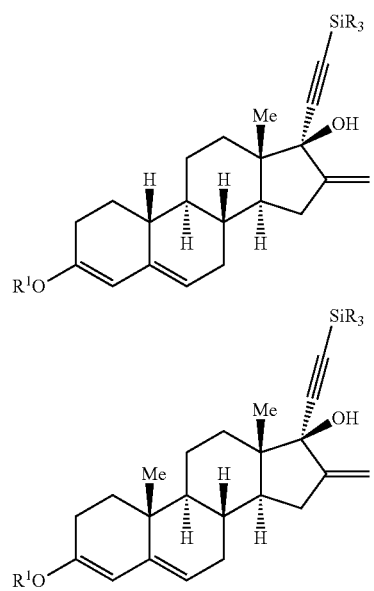

-continued

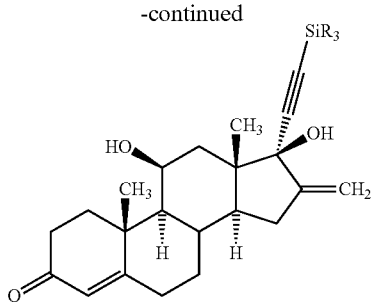

wherein

R is as defined above, preferably, each R is independently selected from $C_1$-$C_6$ alkyl and phenyl, more preferably, each R is independently selected from methyl, iso-propyl and phenyl; and $R^1$ is a substituted or unsubstituted $C_1$-$C_6$ alkyl, preferably a $C_1$-$C_3$ alkyl, more preferably it is selected from methyl and ethyl.

Also, in a particular embodiment, the compound of formula (IV) is a compound of formula (IVa) or (IVa')

(IVa)

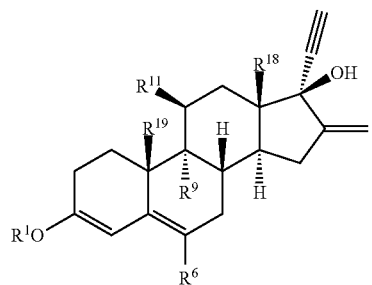

(IVa')

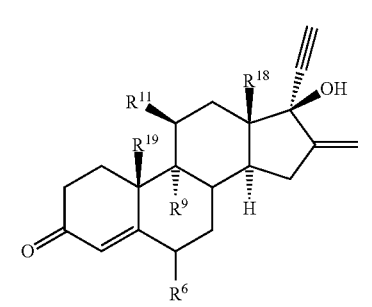

wherein $R^1$, $R^6$, $R^9$, $R^{11}$, $R^{18}$ and $R^{19}$ are as defined above.

Further preferred embodiments for the compounds of formula (IVa) and (IVa') are as those defined previously for (IIa).

Still further preferred compounds of formula (IV) are the following:

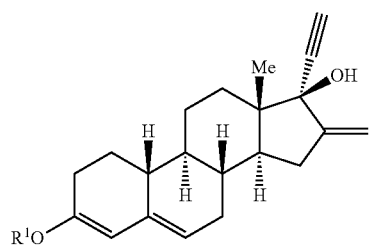

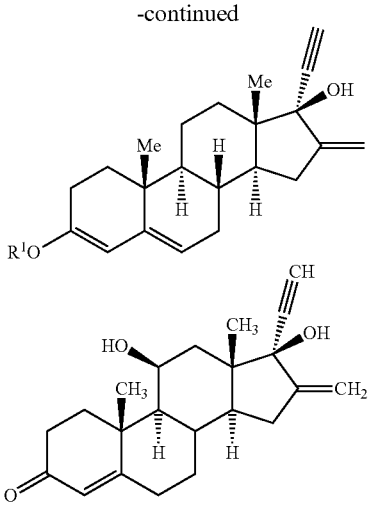

wherein $R^1$ is an optionally substituted $C_1$-$C_6$ alkyl, preferably a $C_1$-$C_3$ alkyl, more preferably it is selected from methyl and ethyl.

The compounds of formula (II) are well known to those skilled in the art or can be readily prepared by methods known in the state of the art (e.g. as disclosed in WO 97/23498, U.S. Pat. Nos. 3,166,551, 3,516,991, 3,275,666, 3,300,521, 3,641,069 and 4,416,821).

In a particular embodiment, compounds of formula (II) having a methylene group (=$CH_2$) at position 16 can be prepared by reacting a compound of formula (V)

(V)

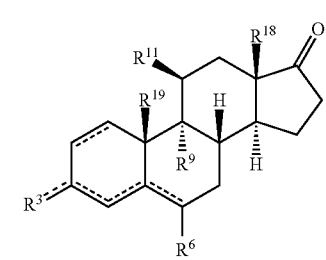

wherein $R^3$, $R^6$, $R^9$, $R^{11}$, $R^{18}$, $R^{19}$ and ≡ are as defined above, with dimethyl or diethyl oxalate in the presence of a base (e.g. an alkaline metal alkanoate, such as sodium methoxide or sodium ethoxide) and, subsequently, with formaldehyde in the presence of acetic acid and triethylamine. In an embodiment, the reaction is carried out at a temperature between −20 and +50° C., preferably between −10 and +20° C., more preferably between −5 and +10° C.

The 16-methylene-17α-ethynyl-17β-hydroxy steroids obtained by the ethynylation process of the invention are useful intermediates in the preparation of several pharmaceutically active agents, such as e.g. Nestorone®, nestorone alcohol or melengestrol acetate. Therefore, in another aspect, the invention is directed to the use of compounds of formula (III) as defined herein in the preparation of Nestorone®, nestorone alcohol or melengestrol acetate.

In a further aspect the invention is directed to a process for the preparation of Nestorone®, nestorone alcohol or melengestrol acetate, which comprises the ethynylation process of the invention.

Processes for converting 16-methylene-17α-ethynyl-17β-hydroxy steroids to said pharmaceutically active compounds are well known to those skilled in the art. For instance, compounds of formula (IV) can be converted to Nestorone®, nestorone alcohol and melengestrol acetate by following the methods disclosed e.g. in U.S. Pat. No. 4,614,621 and WO 97/23498.

In a particular embodiment, compounds of formula (IVa-1)

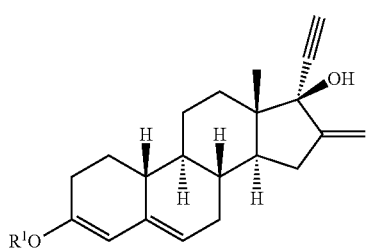

(IVa-1)

wherein R¹ is as defined herein;

can be further converted to Nestorone® following methods known to those skilled in the art. For instance, following a similar synthetic procedure as that disclosed in WO 97/23498 (examples 4-14) and in U.S. Pat. No. 4,614,621 (examples 5-8).

In an embodiment, Nestorone alcohol and Nestorone® can be obtained from a compound of formula (IVa-1) by a process which comprises:

(a) hydrolyzing the enol ether and hydrating the ethynyl group to afford a compound of formula 6

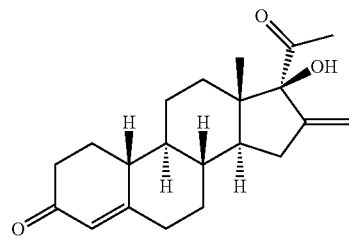

(6)

(b) reacting compound 6 with a phenylsulfenylating agent to afford a compound of formula 7

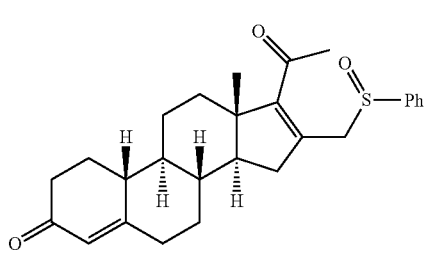

(7)

(c) reacting compound 7 with a thiophilic reagent to afford a compound of formula 8 (Nestorone alcohol)

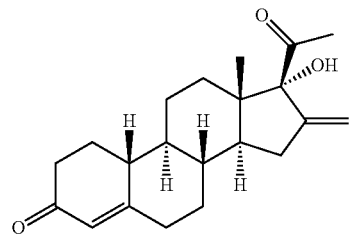

(8)

(d) acetylating the compound of formula 8 to afford Nestorone® (9)

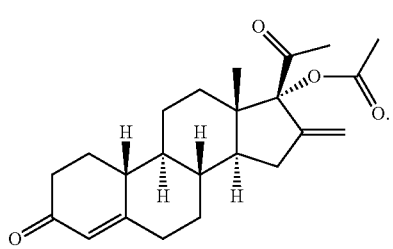

(9)

In a particular embodiment, step (a) above is performed by treating a compound of formula (IVa-1) with an acid, preferably an inorganic acid such as sulphuric acid, nitric acid or hydrochloric acid, in the presence of mercury oxide (HgO) and an organic solvent (e.g. acetone).

In a particular embodiment, step (b) above is performed by treating compound 6 with a phenylsulfenylating agent, such as e.g. PhSCl, PhSBr or PhSSPh, in the presence of an organic solvent (e.g. methylene chloride) and a base.

In a particular embodiment, step (c) above is performed by treating compound 7 with a thiophilic reagent, such as e.g. trimethylphosphite, tris(dimethylamino)phosphine, tris(diethylamino)phosphine, thiophenoxide, sodium sulfide, piperidine or pyrrolidine, in the presence of an organic solvent (e.g. an alcohol, such as MeOH).

In a particular embodiment, Nestorone alcohol (compound 8) can be purified by recrystallization in acetone. This purification allows obtaining compound 8 in high yield and purity.

In a particular embodiment, step (d) above is performed by treating compound 8 with an acetylating agent, such as e.g. acetylanhidride or acetylchloride, in the presence of an organic solvent.

In another embodiment, compounds of formula (IVa-2)

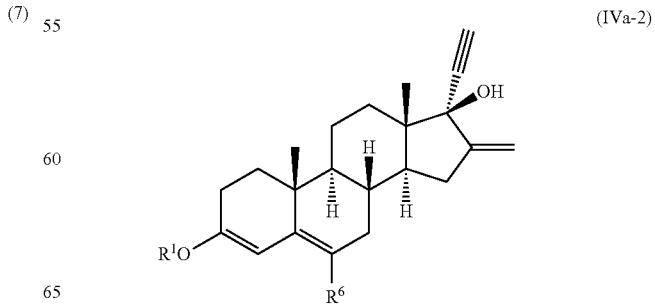

(IVa-2)

wherein
R¹ is as defined herein;
R⁶ is H or Me;
can be further converted to melengestrol acetate following methods known to those skilled in the art. For instance, following a similar synthetic procedure as that disclosed in WO 97/23498 (examples 4-14) and in U.S. Pat. No. 4,614,621 (examples 3-8).

In an embodiment, Melengestrol acetate can be obtained from a compound of formula (IVa-2) wherein $R^6$ is H by a process which comprises:
  steps (a), (b) and (c) as defined for the synthesis of Nestorone®, i.e hydrolyzing the enol ether, hydrating the ethynyl group, reacting the resulting compound with a phenylsulfenylating agent and then with a thiophilic reagent, to afford a compound of formula 10

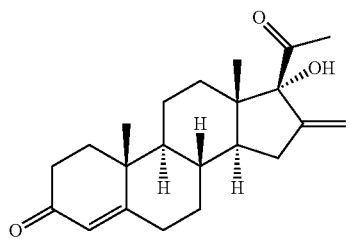

(10)

subjecting compound 10 to a Mannich reaction followed by a Hoffmann elimination to form the exocyclic double bond at position 6, and acetylating to afford compound 11

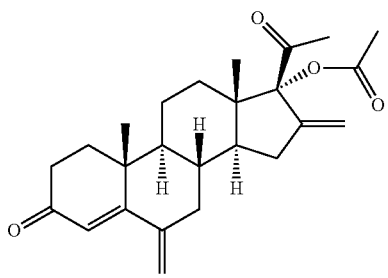

(11)

isomerizing the exocyclic double bond at position 6 in compound II to afford Melengestrol acetate (12)

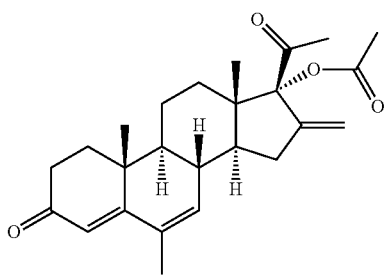

(12)

In a particular embodiment, hydrolysis of the enol ether, hydration of the ethynyl group, treatment with a phenylsulfenylating agent and with a thiophilic reagent, and acetylation reaction can be performed under the conditions defined above for the synthesis of Nestorone®.

Mannich reaction, Hoffmann elimination and isomerization of the exocyclic double bond can be performed by methods known for the skilled person, For instance, following the process disclosed in US 2009/012321.

In a particular embodiment, Mannich reaction can be performed in the presence of a primary or secondary amine such as N,N-dimethylaniline, N-methylaniline, pyrrolidine, piperidine, morpholine, diethylamine, diisopropylamine or N-methylbenzylamine, preferably N,N-dimethylaniline. In an embodiment, Mannich reaction is carried out in the presence of triethyl orthoformate, formaldehyde and N,N-dimethylaniline.

In a particular embodiment, Hoffmann elimination can be performed in the presence of acids such as mineral acids (e.g. hydrogen chloride, sulphuric acid, phosphoric acid) or strong organic acids (e.g. trichloroacetic acid, methanesulphonic acid, trifluoromethanesulphonic acid), preferably in the presence of hydrogen chloride.

In a particular embodiment, isomerization of the exocyclic double bond at position 6 can be performed by hydrogenation in the presence of a palladium/carbon (Pd/C) catalyst.

Compounds of Formula (III)

In another aspect, the invention is directed to a compound of formula (III)

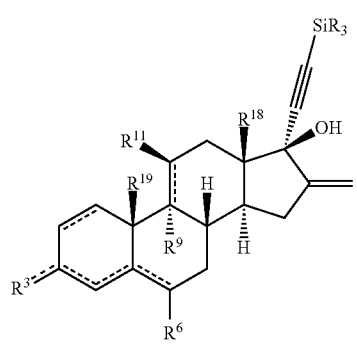

(III)

wherein R, $R^3$, $R^6$, $R^9$, $R^{11}$, $R^{18}$, $R^{19}$ and --- are as defined herein.

In a particular embodiment, the compound of formula (III) is a compound of formula (IIIa) or (IIIa')

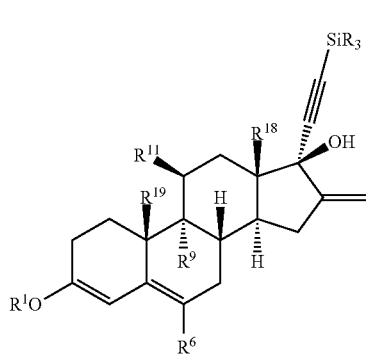

(IIIa)

-continued

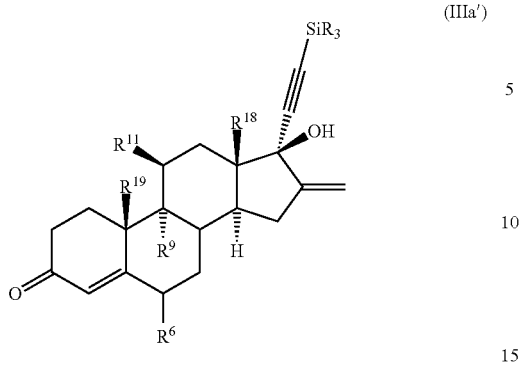
(IIIa')

wherein R, $R^1$, $R^6$, $R^9$, $R^{11}$, $R^{18}$ and $R^{19}$ are as defined above.

In another embodiment, the compound of formula (III) is selected from the following:

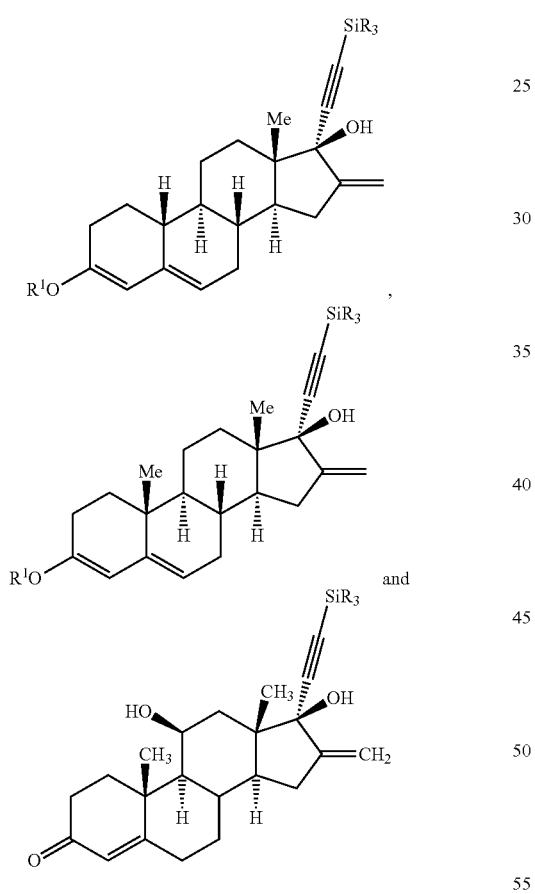

wherein
R is as defined above, preferably, each R is independently selected from $C_1$-$C_6$ alkyl and phenyl. More preferably, each R is independently selected from methyl, iso-propyl and phenyl. In a further embodiment, —$SiR_3$ is selected from $Me_3Si$—, $^iPr_3Si$—, $PhMe_2Si$—; and $R^1$ is an optionally substituted $C_1$-$C_6$ alkyl, preferably a $C_1$-$C_3$ alkyl, more preferably it is selected from methyl and ethyl.

In a further embodiment, the compound of formula (III) is selected from the following:

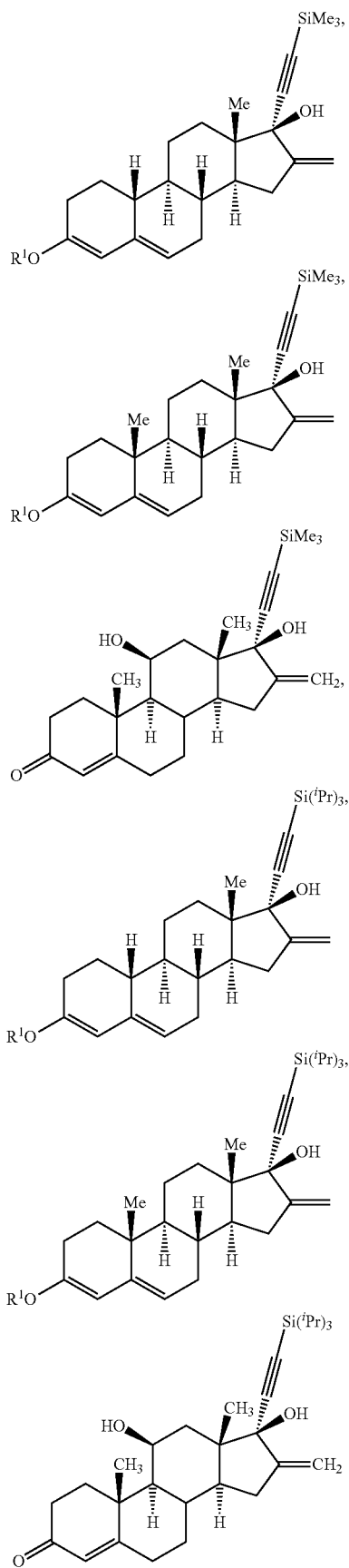

-continued

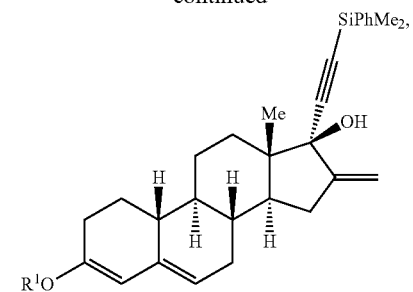

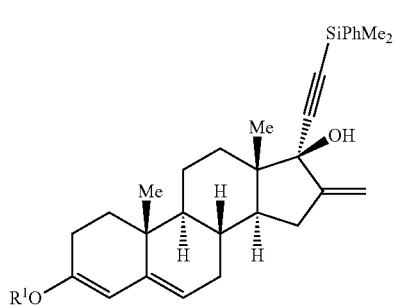
and

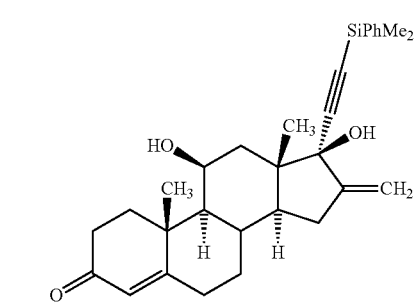

wherein

R¹ is preferably a $C_1$-$C_3$ alkyl, more preferably it is selected from methyl and ethyl.

The following examples illustrate the invention and should not be considered as limitative of the invention.

EXAMPLES

Example 1

Synthesis of 3-ethoxy-16-methylene-18-methyl-19-norandrosta-3,5-dien-17-one (3)

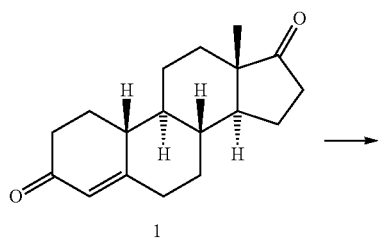

-continued

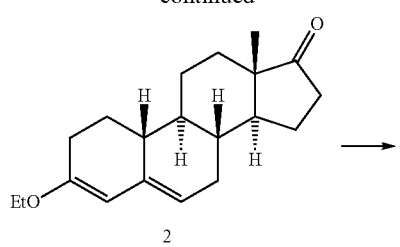

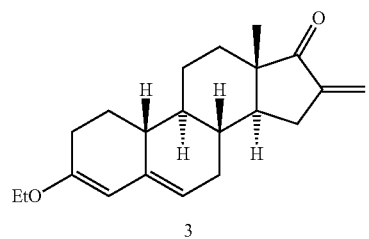

Enol ether (2) was prepared by reacting 19-norandrostendione (1) with trimethyl orthoformate in THF under acid catalysis. Compound (2) was not isolated, but used directly in the next step.

Compound (3) was obtained by treating enol ether (2) with diethyl oxalate and a base. Both sodium methoxide and sodium ethoxide have been used as the base, affording reaction completion in about an hour. Then, acetic acid, methanol and triethylamine and aqueous formaldehyde were added to the reaction mixture. The reaction was carried out at 0° C. and was complete in about 2 hours (WO 97/23498 discloses that this reaction is preferably performed at 0° C., however it has been observed that the reaction proceeds at lower temperature, such as 0° C., affording the desired product with fewer impurities). Then, water was added and the solvent was evaporated under vacuum. The resulting solid was filtered, washed with water and dried. It can be optionally purified by recrystallization in a mixture MeOH/$H_2O$ 6/1 affording compound (3) in 80% yield.

Compound (3), 16-methylen-norAD, is a commercial product well known in the state of the art and disclosed in U.S. Pat. Nos. 3,275,666 and 3,300,521.

Example 2

Synthesis of 3-ethoxy-16-methylene-17α-ethynyl-17β-hydroxy-18-methyl-19-norandrosta-3,5-diene (4)

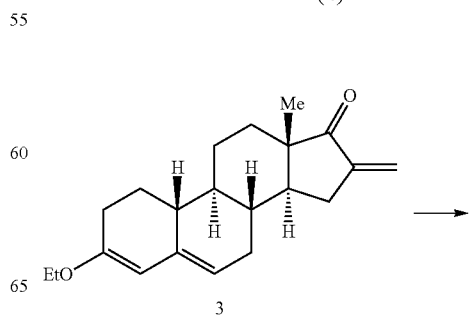

-continued

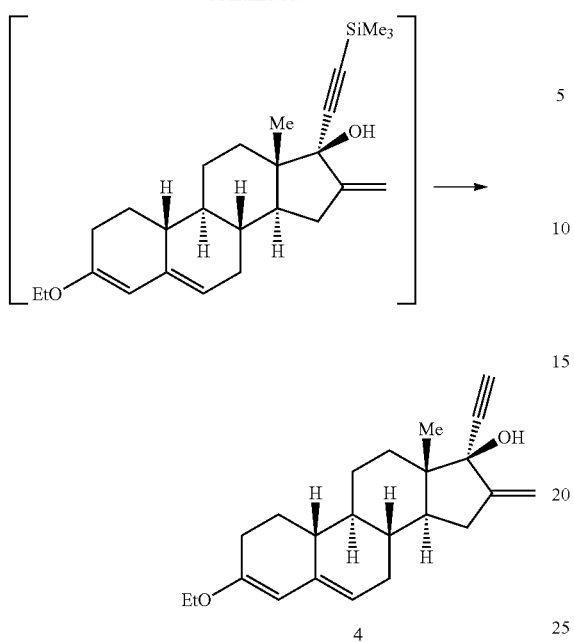

24.5 mL of THF were added to a round-bottom flask under inert atmosphere and cool to −5/−10° C. Then, trimethylsilylacetylene (1.6 equiv.) was added followed by dropwise addition of HMDSLi 1.3 M (1.8 equiv.).

The mixture was stirred at −5/−10° C. for 30 minutes. Then, a solution of compound 3 (9.74 g) in THF (39 mL) was added at the same temperature. When the reaction was complete, 49 mL of metanol and 2.14 g of potassium carbonate (0.5 equiv.) dissolved in 13.5 mL of water were added. Temperature was increased to 20-25° C. until the reaction was complete. 29 mL of water were added, and the solvents distilled under vacuum. The resulting solid was filtered, washed with 20 mL of water and dried at 50° C., giving rise to compound 4 in 92% yield.

Example 3

Synthesis of 16-methylene-17α-acetyl-17β-hydroxy-18-methyl-19-norandrosta-4-en-3-one (6)

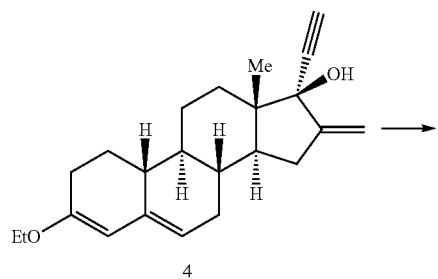

-continued

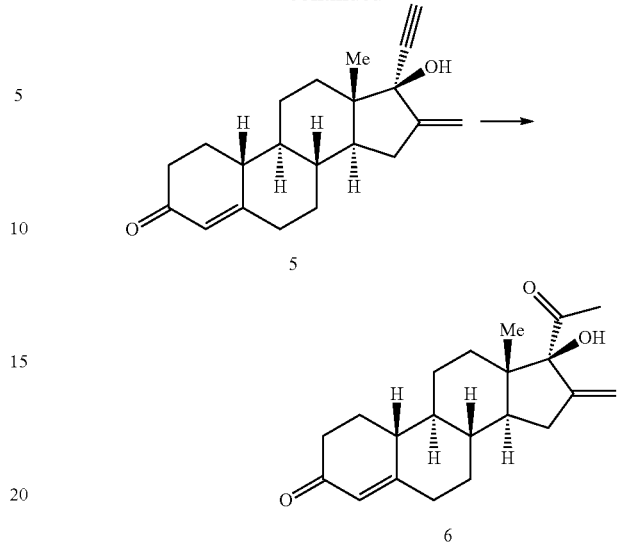

Compound (5) was obtained by treating a solution of compound (4) in acetone with a solution of sulphuric acid and HgO in water. Intermediate (5) was formed by hydrolysis of the enol ether and, without isolation, it was maintained at 65° C. for 1 hour to give rise to the hydration of the ethynyl group to methylketone. When the reaction was complete, mercury salts were removed. The reaction mixture was neutralized with ammonia, water was added and acetone was evaporated under vacuum. The mixture was extracted with $CH_2Cl_2$, treated with acetic acid and Zn to remove mercury residues.

Compound (6) was isolated with high purity (more than 99% by HPLC), so that further purification is not needed.

Example 4

Synthesis of 16-phenylsulfinylmethylene-18-methyl-19-norpregna-4,16-diene (7)

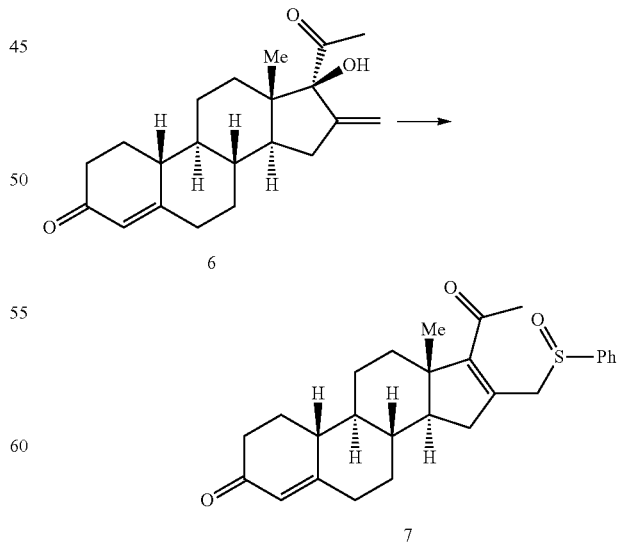

A solution of phenylsulfenyl chloride (1.6 equiv.) in $CH_2Cl_2$ was added to compound (6). Reaction was performed at a temperature of −20° C.±5° C. and catalytic DMAP (0.2 equiv.) and Et₃N (3 equiv.) were employed. When the reaction was complete, excess of PhSCl was removed with MeOH and further addition of HCl 10%. The mixture was decanted, washed with NaHCO₃ to remove acid residues and the solvent was replaced by methanol through distillation.

Example 5

Synthesis of 16-methylene-17α-hydroxy-18-methyl-19-norpregn-4-en-3-one (8)

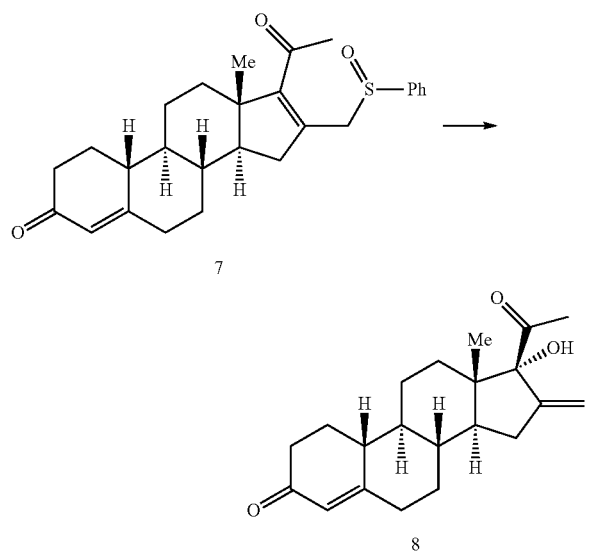

Reaction was performed in the presence of trimethylphsphite (4 equiv.) and Et₃N (0.6 equiv.) and MeOH as solvent in an optimum ratio of 8 L/Kg of compound (7) at 65° C. for 14 h. When the reaction was complete, it was cooled to 10° C. and Nestorone alcohol (8) precipitated as a white solid. HCl 10% was added, it was neutralized and methanol was removed under vacuum. The mixture was extracted with CH₂Cl₂, solvent was removed and acetone was added to purify compound (8) by crystallization.

Example 6

Ethynylation Reaction with Trimethylsilylacetylene and Isolation of the Silylethynyl Intermediate

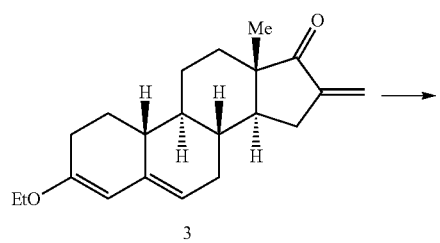

-continued

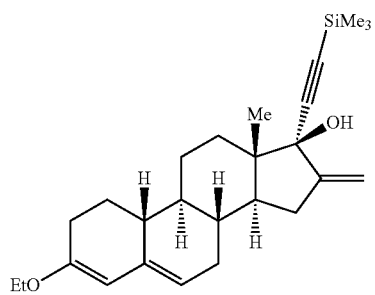

67.5 mL of a solution of HMDSLi 1.3 M in THF were dropwise added to a solution of 11.4 mL of trimethylsilylacetylene (80 mmol) and 37.5 mL of anhydrous THF at −10° C. under inert atmosphere. The resulting mixture was stirred for 30 minutes to form the anion. Then, a solution of compound 3 (15 g, 48 mmol) in anhydrous THF (60 mL) was added. When the reaction was complete (about 30 min.), 90 mL of an aqueous solution of ammonium chloride 12% were added and the phases were separated. Solvent was distilled from the organic phase until a residue was obtained, yielding 19.5 g of 3-ethoxy-16-methylene-17α-trimethylsilylethynyl-17β-hydroxy-19-norandrosta-3,5-diene as an oil (99% yield). The resulting oil is pure enough to be used directly in the next reaction or can be purified by column chromatography.

$^1$H NMR (400 MHz; CDCl₃): δ 0.75 (3H, s, H18); 0.11 (9H, (Si—CH₃)); 1.25 (3H, m, (CH₂—CH₃)); 3.71 (2H, m, (CH₂—CH₃)); 5.16 (1H, s, H4); 5.25 (1H, s, H6); 5.01-5.32 (2H, s, exocyclic CH₂).

$^{13}$C NMR (100 MHz; CDCl₃): δ 0.02 (Si—CH₃); 12.6 (CH₃, C18); 14.6 (CH₂—CH₃); 26.5; 27.2; 28.9; 30.3; 31.0; 32.1; 37.1; 41.5; 43.8; 47.2; 47.1; 62.2 (CH₂—CH₃); 67.8 (C, C21); 80.8 (C, C17); 90.2 (C, C20); 99.7 (CH, C4); 109.1 (CH₂, exocyclic); 117.3 (CH₂, C6); 136.2 (C, C5); 154.1 (C, C3); 156.9 (C, C16).

Example 7

Ethynylation Reaction with Triisopropylsilylacetylene and Isolation of the Silylethynyl Intermediate

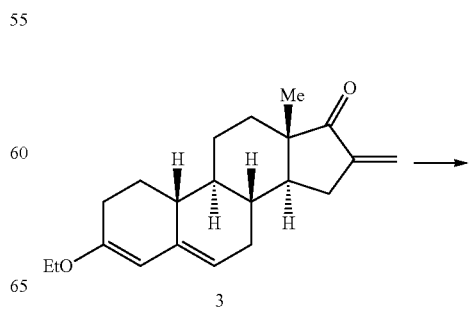

-continued

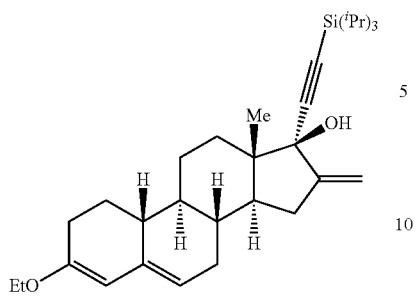

4.5 mL of a solution of HMDSLi 1.3 M in THF were dropwise added to a solution of 0.54 mL of triisopropylsilylacetylene (3.64 mmol) and 3.0 mL of anhydrous THF at −5° C. under inert atmosphere. The resulting mixture was stirred for 30 minutes to form the anion. Then, a solution of compound 3 (1 g, 3.2 mmol) in anhydrous THF (4 mL) was added. When the reaction was complete (about 30 min.), 3 mL of an aqueous solution of ammonium chloride 12% were added and the phases were separated. Solvent was distilled from the organic phase until an oil was obtained, yielding 1.27 g of 3-ethoxy-16-methylene-17α-triisopropylsilylethynyl-17β-hydroxy-19-norandrosta-3,5-diene as an oil (81% yield). The resulting oil is pure enough to be used directly in the next reaction or can be purified by column chromatography.

$^1$H NMR (400 MHz; $(CD_3)_2SO$): δ 0.64 (3H, s, H18); 1.01 (18H, (Si—CH($\underline{CH_3}$)); 1.14 (3H, m, ($CH_2$—$\underline{CH_3}$)); 3.69 (2H, m, ($\underline{CH_2}$—$CH_3$)); 5.16 (1H, s, H4); 5.22 (1H, s, H6); 4.89-5.48 (2H, s, exocyclic).

$^{13}$C NMR (100 MHz; $(CD_3)_2SO$): δ 10.8 (Si—CH($\underline{CH_3}$)$_2$); 12.6 ($CH_3$, C18); 14.0 (Si—$\underline{CH}$($CH_3$)$_2$); 14.4 ($CH_2$—$\underline{CH_3}$); 26.7; 25.9; 28.3; 29.7; 30.8; 31.7; 36.5; 40.7; 43.7; 46.7; 46.6; 61.8 ($\underline{CH_2}$—$CH_3$); 55.9 (C, C22); 79.7 (C, C17); 84.3 (C, C21); 99.6 (CH, C4); 110.7 ($CH_2$, exocyclic); 116.9 ($CH_2$, C6); 135.6 (C, C5); 154.6 (C, C3); 155.7 ($CH_2$, C16).

Example 8

Ethynylation Reaction with Dimethylphenylsilylacetylene and Isolation of the Silylethynyl Intermediate

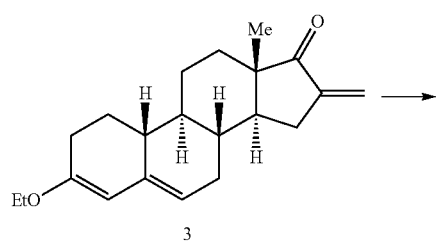

-continued

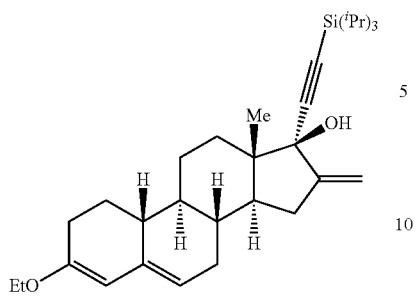

4.5 mL of a solution of HMDSLi 1.3 M in THF were dropwise added to a solution of 0.50 mL of dimethylphenylsilylacetylene (3.4 mmol) and 3.0 mL of anhydrous THF at 0° C. under inert atmosphere. The resulting mixture was stirred for 30 minutes to form the anion. Then, a solution of compound 3 (1.0 g, 3.2 mmol) in anhydrous THF (4 mL) was added. When the reaction was complete (about 30 min.), 0.5 mL of water were added and the mixture was stirred at 15° C. for about 30 min. Then, 3 mL of an aqueous solution of ammonium chloride 12% were added and the phases were separated. Solvent was distilled from the organic phase until an oil was obtained, yielding 1.49 g of 3-ethoxy-16-methylene-17α-dimethylphenylsilylethynyl-17β-hydroxy-19-norandrosta-3,5-diene as an oil (98% yield). The resulting oil is pure enough to be used directly in the next reaction or can be purified by column chromatography.

$^1$H NMR (400 MHz; $(CD_3)_2SO$): δ 0.26 (6H, s, (Si—($\underline{CH_3}$)); 0.64 (3H, s, H18); 1.16 (3H, m, ($CH_2$—$\underline{CH_3}$)); 3.67 (2H, m, ($\underline{CH_2}$—$CH_3$)); 5.15 (1H, s, H4); 5.22 (1H, s, H6); 4.91-5.17 (2H, s, exocyclic); 7.32-7.49 (5H, m, Ph)

$^{13}$C NMR (100 MHz; $(CD_3)_2SO$): δ 0.8 (Si—($\underline{CH_3}$)); 12.7 ($CH_3$, C18); 14.6 ($CH_2$—$\underline{CH_3}$); 26.7; 25.9; 28.4; 29.9; 30.6; 31.9; 36.5; 40.8; 43.5; 46.6; 61.9 ($CH_2$—$CH_3$); 75.6 (CH, C22); 79.1 (C, C17); 86.1 (C, C21); 99.8 (CH, C4); 108.4 ($CH_2$, exocyclic); 117.1 ($CH_2$, C6); 127.8-132.7 (Ph); 135.6 (C, C5); 154.2 (C, C3); 155.7 ($CH_2$, C16); 170.4 (Ph).

Example 9

Ethynylation Reaction Using Lithium Acetylide-Ethylendiamine Complex (Comparative)

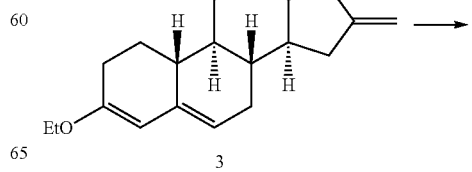

-continued

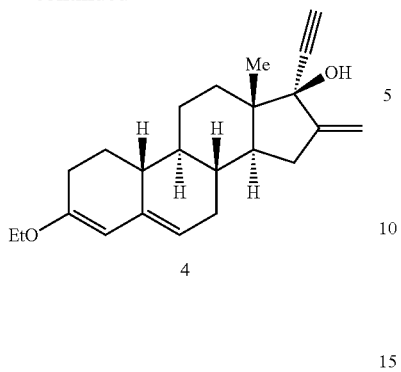

4

A suspension of acetylide-ethylendiamine complex (6 g, 65.2 mmol—commercially available from Aldrich) in 25 mL of THF, was added to a solution of compound 3 (5 g, 16 mmol) in 50 mL of THF at −30° C. The resulting mixture was stirred at the same temperature for 3 h (at that moment, 5.4% of unreacted starting material was observed by HPLC) and then hydrolyzed by the addition of 75 mL of an aqueous solution of NH$_4$Cl 12%. The two phases were separated. The aqueous phase was extracted with AcOEt, the organic phases were combined and the solvent evaporated. The product was isolated in AcOEt and dried to yield 1.8 g of compound 4 (33% yield) together with 0.55% of dimerized product.

Example 10

Ethynylation Reaction Using Ethynyl Magnesium Chloride (Comparative)

A solution of 7 g of compound 3 (22.4 mmol) in 35.5 mL of THF at 5° C., was added to a solution of 84 mL of ethynyl magnesium chloride (0.56M, 47 mmol) in THF at the same temperature. The resulting mixture was stirred at the same temperature for 5 h and then hydrolyzed by the addition of an aqueous solution of NH$_4$Cl 12%. The two phases were separated. The organic phase was washed with brine, and the solvent was evaporated. The product was isolated in acetone and dried to yield 3.73 g of compound 4 (49% yield).

Example 11

Ethynylation Reaction Using Ethynyl Magnesium Chloride and Lanthanum Trichloride (LaCl$_3$*2LiCl) (Comparative)

10 mL of a solution of lanthanum trichloride-LiCl complex (0.6 M, 6 mmol) were added to a solution of 5 g of compound 3 (16 mmol) in 23 mL of THF at 5° C. The mixture was cooled to 0° C. and a solution of 48 mL of ethynyl magnesium chloride (0.56M, 26.9 mmol) was added maintaining the temperature below 10° C. When the reaction was complete, it was hydrolyzed by the addition of 100 mL of a solution of acetic acid in water 10%. The two phases were separated. The organic phase was washed with brine, and the solvent was evaporated. The product was isolated in acetone and dried to yield 2.63 g of compound 4 (48% yield).

What is claimed is:

1. Process for the preparation of a compound of formula (IV)

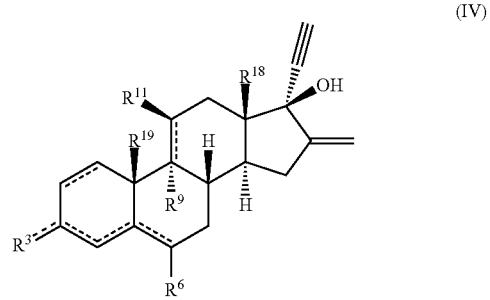

wherein $R^3$ is selected from O and —OR$^1$, wherein R$^1$ is substituted or unsubstituted C$_1$-C$_6$ alkyl; with the proviso that when R$^3$ is O then there are double bonds between C$_3$ and R$^3$ and between C$_4$ and C$_5$ and single bonds between C$_3$ and C$_4$ and between C$_5$ and C$_6$, and when R$^3$ is —OR$^1$ then there are single bonds between C$_3$ and R$^3$ and between C$_4$ and C$_5$ and double bonds between C$_3$ and C$_4$ and between C$_5$ and C$_6$;

$R^6$ is selected from H, substituted or unsubstituted C$_1$-C$_6$ alkyl, halogen and methylene; with the proviso that when R$^6$ is methylene then there is a double bond between C$_6$ and R$_6$ and a single bond between C$_5$ and C$_6$;

$R^9$ is selected from H and halogen, or is absent when there is a double bond between C$_9$ and C$_{11}$;

$R^{11}$ is selected from H, OH and halogen, or is absent when there is a double bond between C$_9$ and C$_{11}$;

$R^{18}$ is selected from methyl and ethyl;

$R^{19}$ is selected from H and methyl;

--- is a single or double bond, which comprises:

(a) reacting a compound of formula (II)

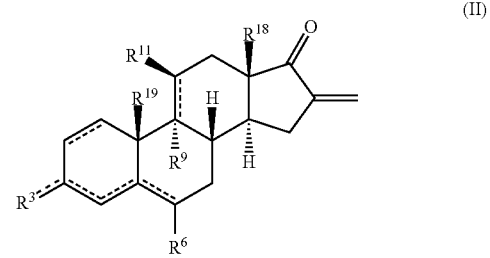

with a compound of formula (I)

wherein each R is independently selected from substituted or unsubstituted C$_1$-C$_6$ alkyl, substituted or unsubstituted aryl and halogen, to afford a compound of formula (III)

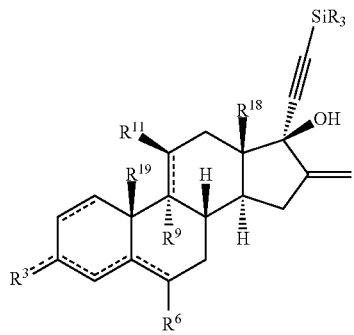

and (b) desilylating the compound of formula (III) to afford a compound of formula (IV).

2. Process according to claim 1, wherein the compound of formula (IV) is a compound of formula (IVa) or (IVa')

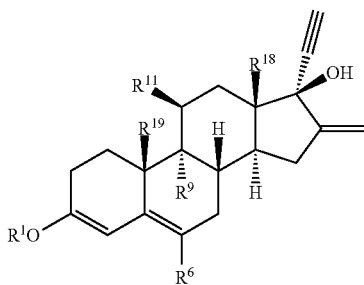

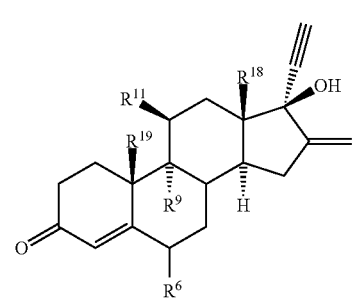

wherein $R^1, R^6, R^9, R^{18}$ and $R^{19}$ are as defined in claim 1.

3. Process according to claim 1, wherein $R^3$ is selected from O or —$OR^1$, wherein $R^1$ is a $C_1$-$C_3$ alkyl;

$R^6$ is selected from H, F, methyl and methylene;

$R^9$ is selected from H and F;

$R^{11}$ is selected from H and OH, or there is a double bond between $C_9$ and $C_{11}$ and $R^9$ and $R^{11}$ are absent;

$R^{18}$ is selected from methyl and ethyl;

$R^{19}$ is selected from H and methyl.

4. Process according to claim 1, wherein the compound of formula (IV) is selected from

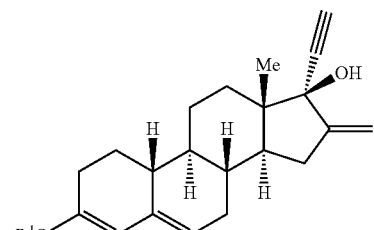

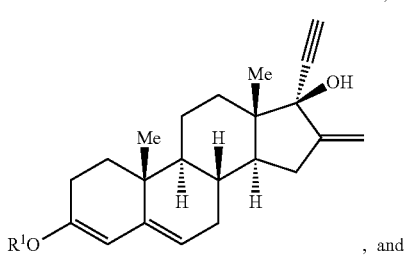

, and

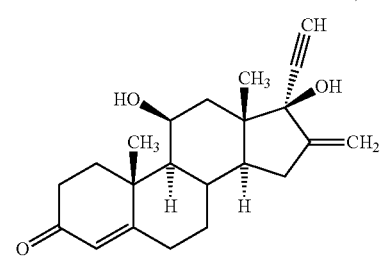

wherein $R^1$ is $C_1$-$C_3$ alkyl.

5. Process according to claim 1, wherein each R is independently selected from $C_1$-$C_3$ alkyl and phenyl.

6. Process according to claim 1, wherein the compound of formula (I) is lithium trimethylsilylacetylene.

7. Process according to claim 1, wherein desilylation step (b) is performed by treatment with potassium carbonate.

8. Process according to claim 1, wherein the ethynylated product is further converted to a compound selected from the group formed by Nestorone®, nestorone alcohol and melengestrol acetate.

9. Process for the preparation of Nestorone alcohol according to claim 8, which comprises the following steps:

(a) treating a compound of formula (IIa-1)

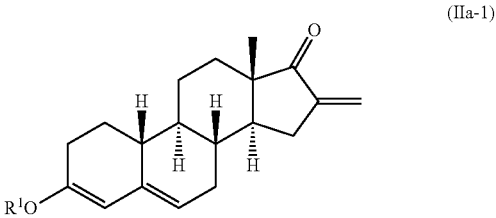

with a compound of formula (I)

$$Li\text{———}\equiv\text{———}SiR_3 \quad (I)$$

to afford a compound of formula (IIIa-1)

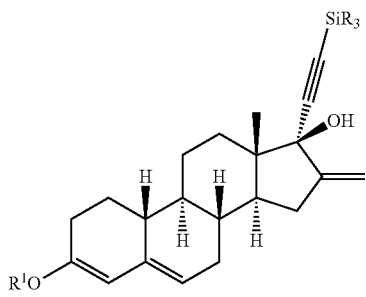

(b) desilylating the compound of formula (IIIa-1) to afford a compound of formula (IVa-1)

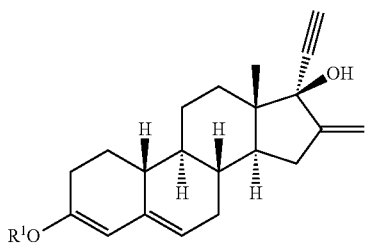

(c) hydrolyzing the enol ether and hydrating the ethynyl group in the compound of formula (IVa-1) to afford a compound of formula 6

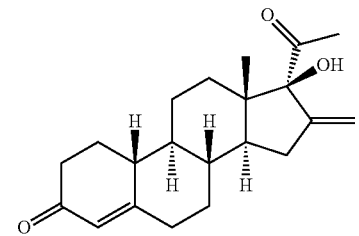

(d) reacting the compound 6 with a phenylsulfenylating agent to afford a compound of formula 7

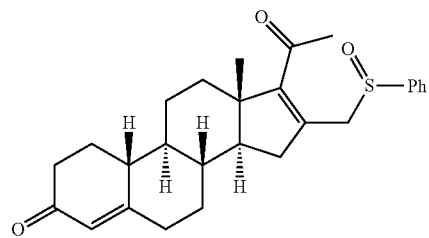

(e) reacting compound 7 with a thiophilic reagent to afford the compound of formula 8 (Nestorone® alcohol)

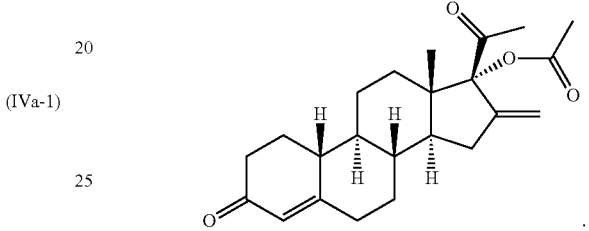

10. Process according to claim 9, which further comprises acetylating the compound of formula 8 to afford Nestorone® (9)

11. Process according to claim 1, comprising one of the following conditions (a) to (d):

(a) wherein each R is independently selected from $C_1$-$C_3$ alkyl and phenyl;

(b) wherein the compound of formula (I) is lithium trimethylsilylacetylene;

(c) wherein desilylation step (b) is performed by treatment with potassium carbonate;

(d) wherein the ethynylated product is further converted to a compound selected from the group formed by Nestorone®, nestorone alcohol and melengestrol acetate.

12. Process according to claim 2, comprising one of the following conditions (a) to (f):

(a) wherein $R^3$ is selected from O or —$OR^1$, wherein $R^1$ is a $C_1$-$C_3$ alkyl;

$R^6$ is selected from H, F, methyl and methylene;

$R^9$ is selected from H and F;

$R^{11}$ is selected from H and OH, or there is a double bond between $C_9$ and $C_{11}$ and $R^9$ and $R^{11}$ are absent;

$R^{18}$ is selected from methyl and ethyl; and $R^{19}$ is selected from H and methyl;

(b) wherein the compound of formula (IV) is selected from

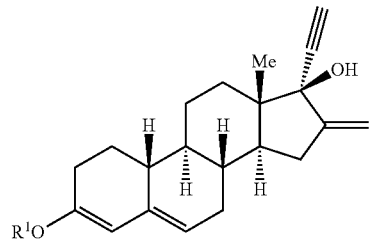

-continued

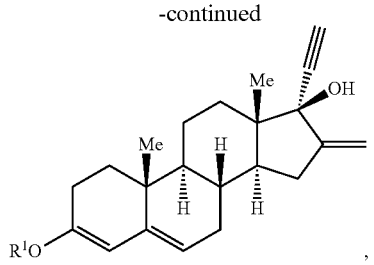

, and

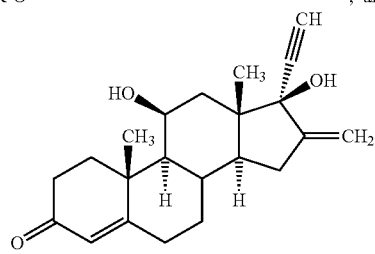

wherein $R^1$ is $C_1$-$C_3$ alkyl;
(c) wherein each R is independently selected from $C_1$-$C_3$ alkyl and phenyl;
(d) wherein the compound of formula (I) is lithium trimethylsilylacetylene;
(e) wherein desilylation step (b) is performed by treatment with potassium carbonate;
(f) wherein the ethynylated product is further converted to a compound selected from the group formed by Nestorone®, nestorone alcohol and melengestrol acetate.

* * * * *